US006185458B1

(12) United States Patent
Ochs et al.

(10) Patent No.: US 6,185,458 B1
(45) Date of Patent: Feb. 6, 2001

(54) REDUCED ENERGY SELF TEST OPERATION IN A DEFIBRILLATOR

(75) Inventors: Dennis E. Ochs, Bellevue; Daniel J. Powers, Issaquah, both of WA (US)

(73) Assignee: Agilent Technologies, Inc., Palo Alto, CA (US)

( * ) Notice: Under 35 U.S.C. 154(b), the term of this patent shall be extended for 0 days.

(21) Appl. No.: 09/302,983

(22) Filed: Apr. 30, 1999

(51) Int. Cl.[7] ....................................................... A61N 1/39
(52) U.S. Cl. .................................................................. 607/5
(58) Field of Search ................................ 607/4–8, 27, 29

(56) References Cited

U.S. PATENT DOCUMENTS

| 4,328,808 | 5/1982 | Charbonnier et al. ............... 128/419 |
| 5,111,813 | 5/1992 | Charbonnier et al. ............... 128/419 |
| 5,285,779 | 2/1994 | Cameron et al. ....................... 607/5 |
| 5,384,544 | 1/1995 | Flugstad et al. ..................... 324/678 |
| 5,395,394 | 3/1995 | Cameron ................................. 607/5 |
| 5,591,213 | 1/1997 | Morgan .................................. 607/5 |
| 5,716,381 * | 2/1998 | Reggiardo .............................. 607/8 |
| 5,800,460 | 9/1998 | Powers et al. .......................... 607/5 |
| 5,873,893 | 2/1999 | Sullivan et al. ....................... 607/5 |
| 6,041,254 * | 3/2000 | Sullivan et al. ....................... 607/5 |

* cited by examiner

Primary Examiner—Jeffrey R. Jastrzab

(57) ABSTRACT

A defibrillator having a self test operation requiring reduced energy is provided. During a self test operation of the defibrillator, it is necessary to deliver a test pulse to a test load under appropriate levels of voltage and current stress to the HV circuits. In verifying the functionality of an HV switch under self test, several critical parameters must be evaluated. First, the voltage stress test is conducted at the maximum voltage level to ensure that the dielectric withstand voltage of the various components of the HV circuit are adequate under maximum voltage conditions. Second, the current stress test is conducted at the maximum current level but at a partial voltage which consumes substantially less energy. The maximum voltage and maximum current levels may be chosen to exceed the operating voltage and current levels encountered during normal operation of the defibrillator to more fully test the HV switch.

31 Claims, 6 Drawing Sheets

REDUCED ENERGY SELF TEST OPERATION IN A DEFIBRILLATOR

BACKGROUND OF THE INVENTION

This invention relates to electrotherapy circuits and in particular to a defibrillator having an improved self test operation that requires less energy.

Electro-chemical activity within a human heart normally causes the heart muscle fibers to contract and relax in a synchronized manner that results in the effective pumping of blood from the ventricles to the body's vital organs. Sudden cardiac death is often caused by ventricular fibrillation (VF) in which abnormal electrical activity within the heart causes the individual muscle fibers to contract in an unsynchronized and chaotic way. The only effective treatment for VF is electrical defibrillation in which an electrical shock is applied to the heart to allow the heart's electro-chemical system to re-synchronize itself. Once organized electrical activity is restored, synchronized muscle contractions usually follow, leading to the restoration of cardiac rhythm.

The necessity to apply defibrillation quickly after onset of VF has given rise to automatic external defibrillators (AEDs) which may be used by first responders and lay people. AEDs may remain unused for long periods of time and yet must be ready to operate reliably in an emergency situation. To ensure operational readiness, most AEDs employ a self test operation that is conducted at regular intervals.

The Heartstream Forerunner® AED, for example, employs a self test system that generates self test operations automatically in response to a predetermined schedule. The self test operation typically includes a number of different system checks including functional, calibration, and safety tests to verify that the defibrillator's components and operation are within predetermined specifications. The high voltage (HV) circuit is a critical component of the defibrillator that provides the defibrillation pulse. Verification of the proper functioning of the defibrillator is a typical part of any self test operation.

U.S. Pat. No. 5,591,213, "Defibrillator System Condition Indicator", issued Jan. 7, 1997, to Morgan et al., describes a defibrillator system which includes means for periodically operating a high voltage (HV) circuit to discharge a test pulse to a test load. Such self tests may be done periodically or in response to changes in the defibrillator environment such as the ambient temperature as described in U.S. Pat. No. 5,868,792, issued Feb. 9, 1999, "Environment-Response Method for Maintaining Electronic Devices Such As An External Defibrillator", issued Feb. 9, 1999, to Ochs et al. which is incorporated herein by reference.

U.S. Pat. No. 5,800,460, "Method for Performing Self-Test In A Defibrillator", issued Sep. 1, 1998, to Powers et al., describes in detail the operation of a defibrillator self test system which is incorporated herein by reference. An energy storage capacitor is twice charged to full voltage and discharged, first to functionally verify operation of the HV circuit under combined maximum voltage and current conditions and second to calibrate the HV circuit to ensure that the amount of energy delivered in the defibrillation pulse is within specification limits. The test load is resistance typically in the range of 10 to 20 ohms.

Providing a test pulse to the test load at a combined maximum voltage and maximum current stress as taught in by Powers et al. results in a substantial amount of energy dissipated in the test load for each self test operation. It has been found that over time the periodic self test operations conducted by the AED substantially reduced its battery life. The self test of the HV circuit forms only a portion of the overall defibrillator self test but consumes the majority of total energy that is required.

U.S. Pat. No. 5,873,893, "Method and Apparatus for Verifying the Integrity of an Output Circuit Before and During Application of a Defibrillation Pulse", to Sullivan et al. describes an external defibrillator capable of testing the high voltage output circuit for open and shorted switches by monitoring the energy storage capacitor voltage. The high voltage circuit, the well known H-bridge configuration, is tested first by sequentially turning on each of the switches in each leg of the H-bridge while the energy storage capacitor is charged up to a test voltage. No current conducting paths should appear through the H bridge. Next, current conducting paths through each side of the H bridge are created for a brief time and the energy storage capacitor voltage is monitored. The energy storage capacitor voltage should drop by a predetermined amount for each discharge. While it is mentioned by Sullivan et al. that the test voltage may be less than the maximum voltage to reduce energy consumption, there is no teaching on how the test voltage may differ between the open and short circuit tests to allow for full testing of HV circuit at both maximum current and maximum voltage levels.

It would therefore be desirable to provide a method and apparatus of reduced energy self test in a defibrillator which allows for testing of the HV circuit at both maximum current and maximum voltage.

SUMMARY OF THE INVENTION

In accordance with the present invention, a defibrillator having a self test operation requiring reduced energy is provided. During a self test operation of the defibrillator, it is necessary to deliver a test pulse to a test load under appropriate levels of voltage and current stress to the HV circuits. HV circuits will typically include an energy storage capacitor, a high voltage charger to charge the energy storage capacitor, and an HV switch which operates to deliver a defibrillation pulse to a patient in a desired polarity and for a desired pulse duration using the energy from the energy storage capacitor. In the preferred embodiment, the HV switch is an H-bridge circuit which is well known in the art to commutate the voltage from the energy storage capacitor to the patient first in one polarity and then in the other polarity to form a biphasic defibrillation pulse.

In verifying the functionality of an HV switch during the self test operation, several critical parameters must be evaluated. First, a voltage stress test is conducted to ensure that the dielectric withstand voltage of the various components of the HV switch are adequate at the maximum voltage level. In the preferred embodiment, the components of the HV switch are silicon controlled rectifiers (SCRs) and insulated gate bipolar transistors (IGBTs).

First, the voltage stress test is conducted by imposing the maximum voltage level which would be incurred during normal use, typically 2,000 volts, across each of the components in the HV switch and monitoring either for any current flow through each component or a significant voltage drop in the energy storage capacitor voltage.

Second, the current stress test is conducted to ensure that the current handling capability of each component is adequate to source the maximum current level which would be incurred during normal use, typically 100 amperes, to the test load. The test load is preferably a low impedance that less than the lowest impedance of the expected range of impedances spanning 20 to 200 ohms. The maximum voltage level and the maximum current level may be chosen to exceed the operating voltage level and operating current level which are the maximum values that occur during normal operation of the defibrillator in order to more fully stress the components of the HV switch and charging circuitry.

The present invention allows for testing of the HV circuit at the maximum current level and at the maximum voltage level with substantially reduced energy consumption and battery drain during the self test of the HV circuit from that of the prior art. The current stress test is conducted at substantially lower energy levels by coupling a low impedance test load across the H bridge in place of a patient impedance and with the energy storage capacitor charged to a partial voltage. The voltage stress test is done at the maximum voltage level and on its own consumes no energy because there is no path for the current to flow under normal conditions and is. The charge stored in the energy storage capacitor, which is still at the maximum voltage level following the voltage stress test, can then be used for other portions of the self test operation including generation of the calibration pulse.

One feature of the present invention is to provide a self test method for a defibrillator.

A further feature of the present invention is to provide a method of reduced energy self test in a defibrillator.

A further feature of the present invention is to provide a method of reduced energy self test in a defibrillator that provides for testing at maximum voltage and maximum current levels.

Another feature of the present invention is to provide an external defibrillator having a reduced energy self test circuit.

Other features, attainments, and advantages will become apparent to those skilled in the art upon a reading of the following description when taken in conjunction with the accompanying drawings.

DETAILED DESCRIPTION OF THE INVENTION

Figure 1:
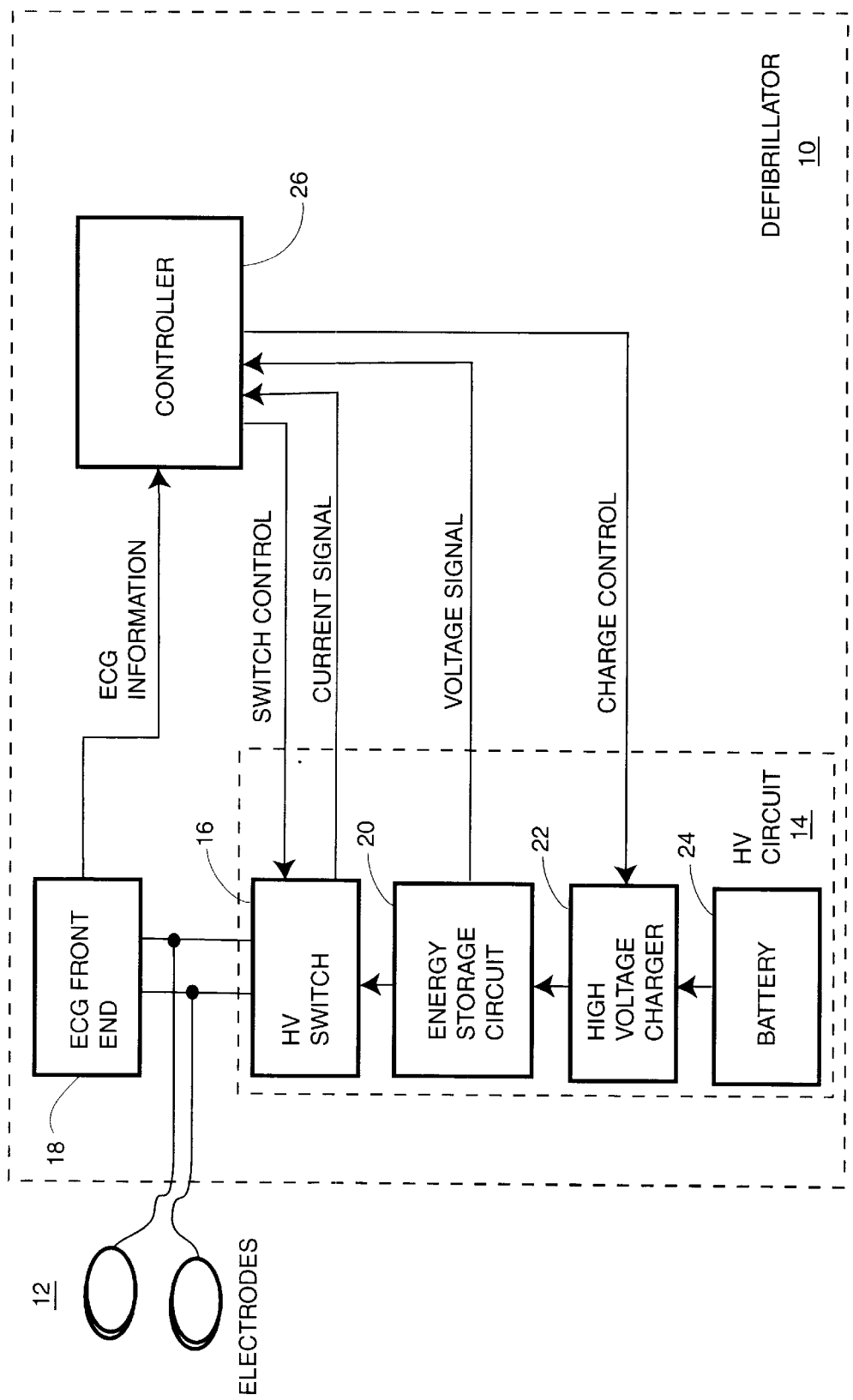
FIG. 1 is a block diagram of a defibrillator having an HV circuit that is tested according to the present invention.

FIG. 1 is a block diagram of a defibrillator 10 that incorporates a method of reduced energy self test according to the present invention. A pair of electrodes 12 are coupled across the chest of a patient (not shown). The pair of electrodes 12 are coupled to an ECG front end 18 which filters, amplifies, and digitizes the ECG signal from the patient to obtain ECG information which is provided to a controller 26. A defibrillation pulse may be delivered to the patient by the defibrillator 10 upon detection of a shockable rhythm such as ventricular fibrillation (VF) that is detected in the ECG information by the controller 26 running a shock advisory algorithm.

An HV circuit 14 is coupled to the electrodes 12 and delivers a defibrillation pulse in a desired polarity and duration across the electrodes 12. In the preferred embodiment, the defibrillation pulse is a biphasic truncated exponential waveform. The HV circuit 14 contains an HV switch 16 that is coupled to the pair of electrodes 12, an energy storage circuit 20 coupled to the HV switch 16, and a high voltage charger 22 for charging the energy storage circuit 20 to the desired charge level. In the preferred embodiment, the HV switch 16 is constructed as an H bridge as explained in more detail below.

The energy storage circuit 20 is coupled to the HV switch 16 to provide the high voltage, high current waveform necessary to develop the defibrillation pulse. The energy storage circuit 20 typically consists of at least one capacitor with a capacitance value in the range of 100 to 200 microFarads (uF) and which is charged to over 2000 volts at the maximum voltage. The high voltage charger 22 converts the relatively low battery voltage, typically 12 volts, from a battery 24 to the relatively high voltage levels required to charge the energy storage circuit 20.

The controller 26, implemented for example with a general purpose microprocessor, an embedded controller, or a state machine, operates to control the functions of the defibrillator 10 including the self test operation according to the present invention. The HV switch 16 develops the defibrillation pulse responsive to a switch control signal from the controller 26 in the desired polarity and pulse duration. The voltage of the energy storage circuit 20 is controlled through via the charge control signal to the high voltage charger 22 from the controller 26. During the self test operation, a current signal from the HV switch 16 and a voltage signal from the energy storage circuit 20 may be fed back to the controller 26 which evaluates the results of the self test operation.

Figure 2:
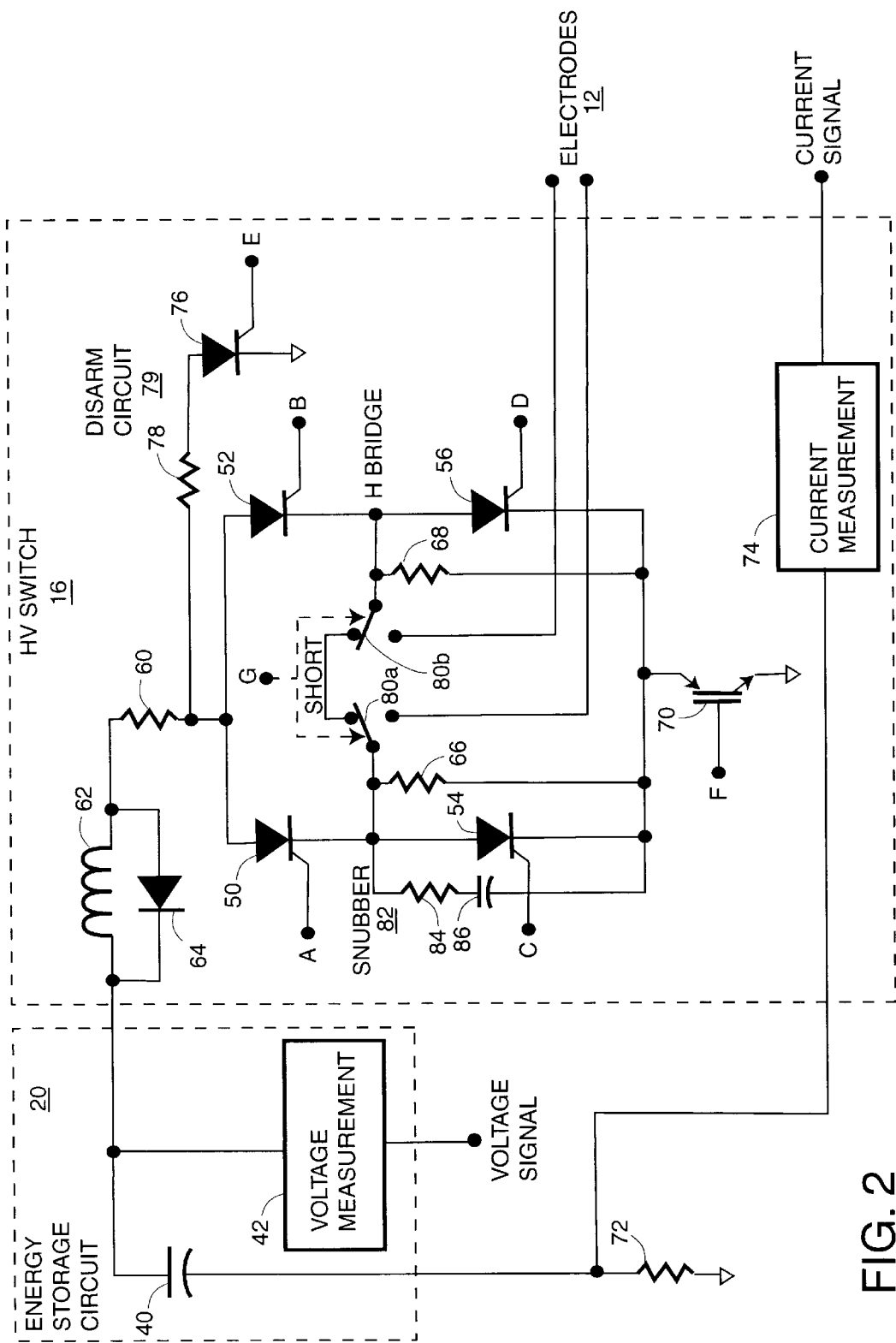
FIG. 2 is a schematic diagram of the HV switch portion of the HV circuit of FIG. 1.

In FIG. 2, there is shown a simplified schematic drawing of the energy storage circuit 20 and the HV switch 16. A capacitor 40 in the energy storage circuit 20 provides for storage of the energy required for the defibrillation pulse. The capacitor 40 is charged to a voltage level determined by the controller 26. The voltage level is measured using a voltage measurement circuit 42 that provides the voltage signal back to the controller 26.

The voltage measurement circuit 42 preferably consists of a voltage divider network and analog to digital converter that provides the voltage signal in the form of digital measurement values to the controller 26. If the voltage signal from the energy storage circuit 20 has a value within specification limits based on the charge control signal to the high voltage charger, then the high voltage charger 22 is determined to be functioning normally.

SCRs 50–56 form an H bridge circuit coupled between the capacitor 40 and ground. The H bridge circuit, under the control of the controller 26 which generates the switch control signals A–F, operates to couple the voltage from the capacitor 40 to the patient in the desired polarity and for the desired time duration. The SCRs 50–56 are controlled via control inputs A–D which each receive the switch control signals A–D from the controller 26. The voltage from the capacitor 40 is coupled to the H bridge circuit via a series resistor 60 and a parallel combination of an inductor 62 and clamping diode 64. The inductor 62 has an inductance value chosen to limit the rate of current change through the H bridge in order to allow current limiting circuits (not shown) time to engage before excessive current flows through the H bridge. The series resistor 60 is in the range of 5 ohms in the preferred embodiment.

Pull down resistors 66 and 68 ensure that the cathode ends of the SCRs 50 and 52 are near ground potential when the SCRs 50 and 52 are off and the IGBT 70 is on. This ground potential is also the normal operating state of the HV switch 16 when the energy storage circuit 20 is charged up and ready to deliver the defibrillation pulse. The resistors 66 and 68 have resistance values that are high enough, for example in the 10,000 ohm range that they draw only nominal current when either of the SCRs 50 or 52 is on.

A snubber circuit 82, consisting of a resistor 84 in series with a capacitor 86, is coupled in shunt across the SCR 54. The snubber circuit 82 is provided to prevent the inadvertent triggering of the SCR 54 responsive to a rapid rise in voltage between the anode and cathode, commonly known as dV/dt trigger. The ability of the snubber circuit 82 to prevent dV/dt trigger may be effectively tested during the voltage stress test by providing a rapidly changing voltage across the SCR 54 such as by turning on one of the SCRs 50 and 52 with the switch 80a–b in the short position.

Interposed between the H bridge and ground is an insulated gate bipolar transistor (IGBT) 70 having a control input F. The control input F receives a portion of the switch control signal from the controller 26. The IGBT 70 operates as a switch to interrupt the flow of current through the H bridge to allow the SCRs 50–56 to turn off. A current measurement circuit 74 measures the current flowing through the H bridge by measuring the voltage across a resistor 72 which is interposed between the capacitor 40 and ground. The current measurement circuit 74 may alternatively consist of an over-current detector in the form of a comparator configured to provide an over-current signal when the current through the H bridge exceeds a predetermined trip level.

A disarm circuit 79 consisting of an SCR 76 with a control input E in series with a load resistor 78 operates in parallel with the H-bridge circuit. The control input E receives a portion E of the switch control signal from the controller 26. The disarm circuit operates to safely discharge the capacitor 40 through the load resistor 78 and the resistor 60 during normal operation of the defibrillator 10 when a defibrillation pulse to the patient is not needed. The disarm circuit may also be used in the self test mode with the load resistor 78 and the resistor 60 operating as the test load to receive the calibration pulse generated by turning on the SCR 78 using the switch control signal E from the controller 26.

The discharge time of the calibration pulse is measured by the controller 26 by monitoring the voltage or current signal in order to control for variations in the charge voltage and capacitance value of the capacitor 40. Using the measured discharge times, the controller 26 may then compensate for variations in voltages and component values in order to deliver a defibrillation pulse to the patient within desired specification limits. Applying the disarm shock through the SCR 76 will also apply the maximum voltage level to the collector of the IGBT 70 which should be in the off state.

At the output of the H bridge is a switch 80a–b which operates as a ganged double pole, double throw switch with an upper and lower position controlled by a control input G. The control input G receives a switch control signal G from the controller 26. In the lower position, the switch 80a–b couples the HV switch 16 to the electrodes 12 in order to deliver a defibrillation shock to the patient. In the upper position, the switch 80a–b couples the H bridge to a short circuit. In the preferred embodiment, the short circuit is an electrical connection such as a short piece of wire with a resistance substantially close to zero ohms and the resistor 60 operates as the test load. Alternatively, the switch 80a–b could couple the H bridge to a test load with the desired test load resistance. In another alternative, the switch 80a–b couples the H bridge to an external resistor (not shown) with a value chosen such that the series combination of the external resistor and the resistor 60 equal the desired test load resistance.

To deliver a biphasic defibrillation pulse to the patient, the capacitor 40 is charged to a desired voltage level and the switch 80a–b is placed in the lower position to couple the HV switch 16 to the pair of electrodes 12. The IGBT 70 is then turned on followed by SCRs 50 and 56 to begin the first phase of the defibrillation pulse that is delivered to the patient. After a desired period of time, the IGBT 70 is turned off followed by the SCRs 50 and 56 to end the first phase. To begin the second phase, the IGBT 70 is again turned on, followed by the SCRs 52 and 54. After a desired period of time, the IGBT 70 is again turned off followed by the SCRs 52 and 54. If a no-shock decision is reached by the controller 26 after the capacitor 40 had been charged, the disarm circuit could be activated by turning on SCR 76 to safely discharge the capacitor 40 through the load resistor 78.

During the self test operation of the defibrillator 10 according to the present invention, a series of tests of the H bridge are conducted in order to ensure its proper function within specified limits. Such tests include current stress, voltage stress, and calibration. The current stress test is conducted at the maximum current level and the voltage stress test is conducted at the maximum voltage level. The self test operation according to the prior art will be explained in more detail below according to FIG. 3. The self test operation according to the present invention will be explained in more detail below according to FIGS. 4 and 6. In an alternative embodiment of the present invention, the maximum voltage and current levels may exceed the current and voltage levels encountered during normal operation of the defibrillator 10 as explained in more detail below according to FIG. 5.

Figure 3:
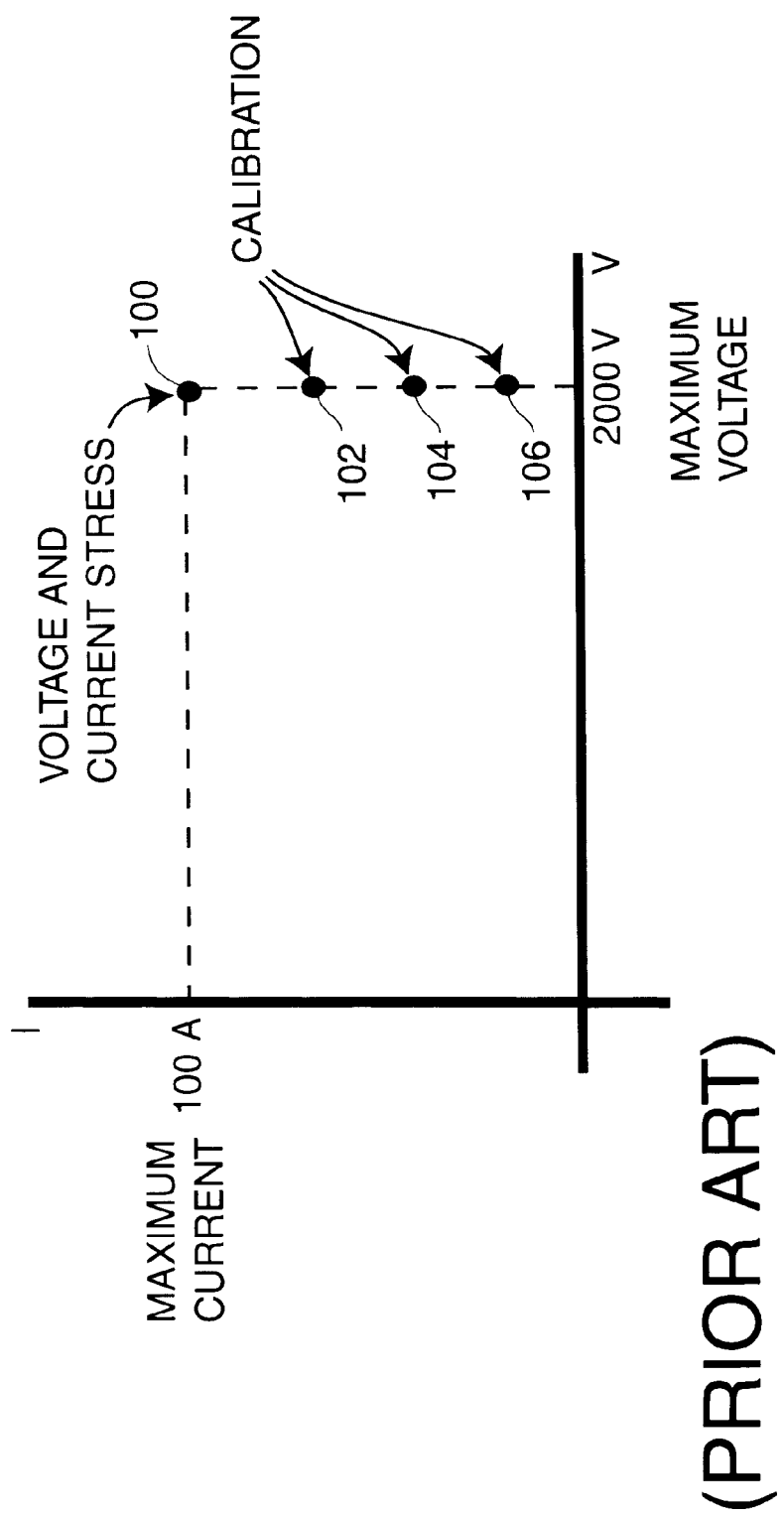
FIG. 3 is a graph of voltage versus current of a combined voltage stress and current stress test as conducted according to prior art self test methods.

FIG. 3 is a graph of voltage versus current for the voltage and current stress tests and calibration tests as conducted according to the prior art. The current stress and voltage stress tests occur simultaneously as the maximum current and maximum voltage conditions are met with discharge into a 20 ohm load which includes 10 ohms of series resistance and 10 ohms test load. This first test corresponds to location 100 on the graph of FIG. 1 with a maximum voltage of 2,000 volts and a maximum current of 100 amperes (A).

Under the self test conditions given in this example, 10 ohms as the test load resistance is the worst case condition occurring below in the expected range of patient impedances which are generally believed to span 20 to 200 ohms. The full amount of energy stored in the energy storage capacitor would be discharged into the two 10 ohm resistors. For example, a 100 uF energy storage capacitor charged to 2,000 volts would have 200 joules (j) of energy according to the formula:

$$\text{energy (j)} = 0.5 \cdot C \cdot V^2$$

where: C is capacitance (in Farads) of the capacitor
V is the charge voltage across the capacitor Next, the energy storage capacitor is again charged up to maximum voltage and a calibration pulse is discharged into the test load corresponding to location 102 on the graph. Other known resistor values may be substituted for the test load resistance corresponding to locations 104 and 106 so that the discharge time for each of the known load resistances may be measured. Using the discharge time measurements and the known resistances to solve a system of equations, the charge voltage and the capacitance of the energy storage capacitor can be determined and then controlled for by compensation in the pulse duration of the defibrillation pulse in order to deliver a desired amount of energy to the patient. While this self test method according to the prior art is effective, it results in two full discharges of the capacitor totaling 400 j using the energy value from the above example, resulting in substantial battery drain for each self test operation.

Figure 4:
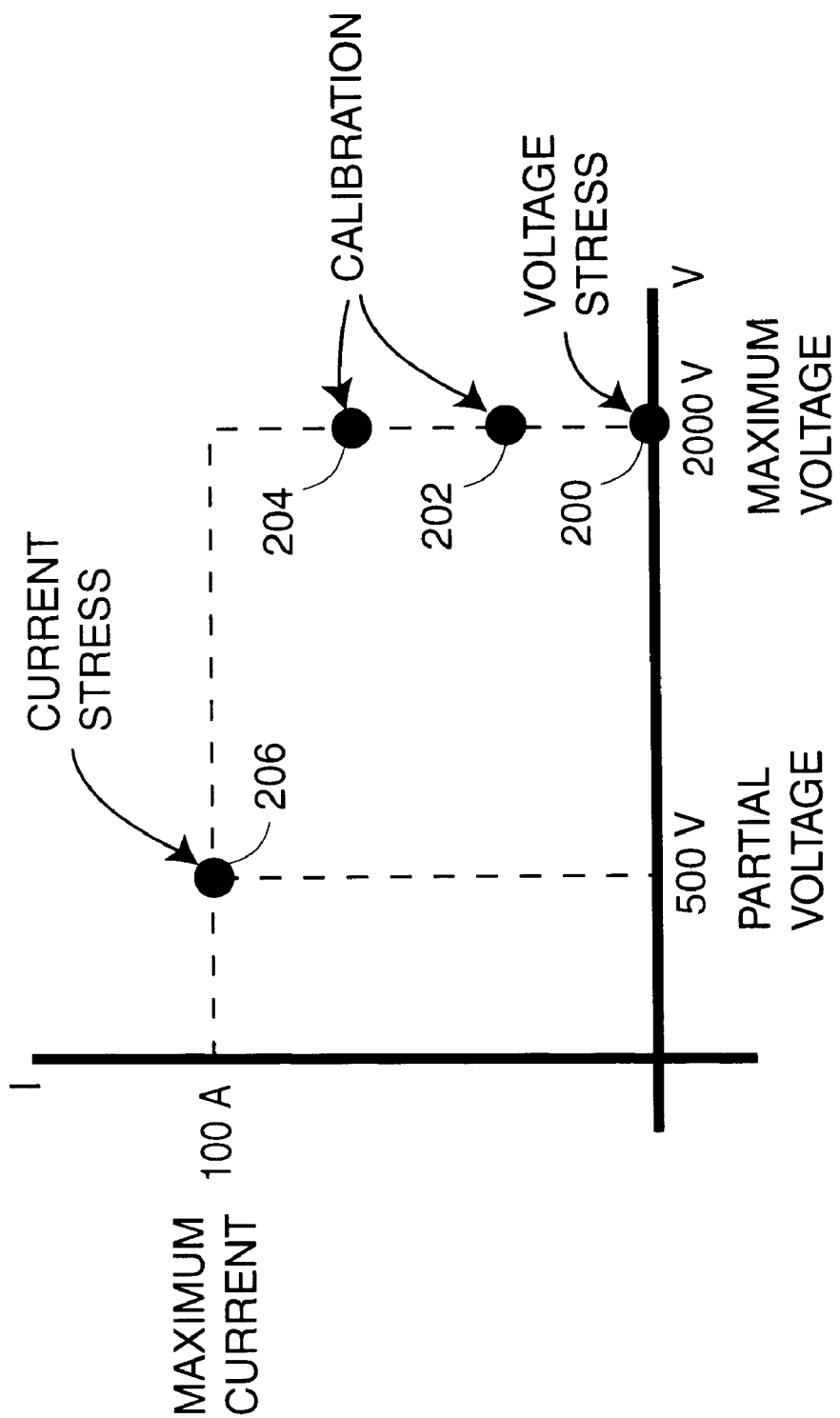
FIG. 4 is a graph of voltage versus current showing the separate voltage stress and current stress tests as conducted according the self test method of the present invention.

FIG. 4 is a graph of voltage versus current for the voltage and current stress tests and calibration tests as conducted according to the present invention. The current stress and voltage stress tests occur separately, along with the calibration portion. According to the present invention, the capacitor 40 is charged to the maximum voltage only once for the voltage stress test which occurs at location 200 on the graph. Since no current flows for a normal voltage stress test, no energy is dissipated and the capacitor 40 remains at the maximum voltage level. Calibration pulses may then be generated and their discharge times measured for calibration purposes at locations 202 and 204 on the graph.

Finally, the capacitor 40 is charged to the partial voltage, for example to 500 volts, to obtain the desired level of current for the current stress test of 100 A with a test load resistance of 5 ohms corresponding to location 206 on the graph. At the partial voltage of 500 volts, the capacitor 40 is storing only ¹⁄₁₆ the amount of energy of the maximum voltage level of 2,000 volts, resulting in substantially reduced energy requirements for self test from that of the prior art.

Figure 5:
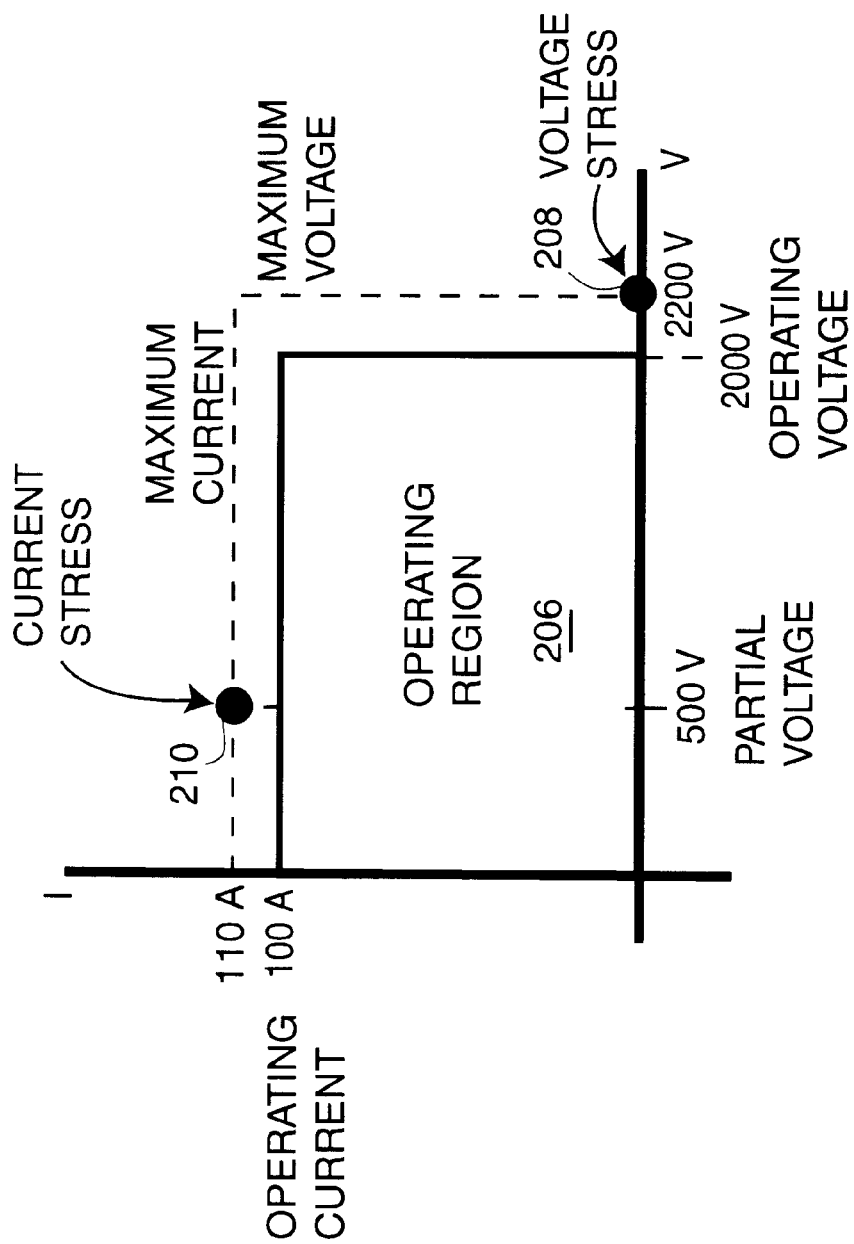
FIG. 5 is a graph of voltage versus current showing an alternative embodiment of the present invention in which the maximum current and voltage exceed the voltage and current of the operating region.

FIG. 5 is a graph of voltage versus current for the voltage and current stress tests and calibration tests as conducted according to an alternative embodiment of the present invention. An operating region 206 is a region which defines as the range of voltages and currents that may be expected during the normal operation of the defibrillator 10 when delivering a defibrillation pulse. The maximum voltage and maximum current, instead of coinciding with the operation voltage and current as in the preferred embodiment, are now chosen to exceed the operating voltage and current.

In the example illustrated in FIG. 5, the maximum current is chosen to exceed the operating current by ten percent and the maximum voltage is chosen to exceed the operating voltage by ten percent. The benefit of exceeding the operating voltage and current during the voltage stress test and current stress test is achieving an added margin of safety in ensuring the proper function of the components of the HV switch 16, energy storage circuit 20, and the high voltage charger 22. The benefits of present invention are realized in the alternative embodiment by obtaining a wider margin of safety in the self test operation while substantially reducing the energy requirements.

The capacitor 40 is charged to maximum voltage level only once for the voltage stress test which occurs at location 208 on the graph. Since no current flows for a normal voltage stress test, no energy is dissipated and the capacitor 40 remains at maximum voltage. The calibration pulses may then be generated and their discharge times measured for calibration purposes preferably at locations within or along the border of the operating region 206.

Finally, the capacitor 40 is charged to the partial voltage, for example to 550 volts, to obtain the desired level of current for the current stress test of 100 A corresponding to location 206 on the graph. At the partial voltage of 550 volts, the capacitor 40 is storing only ¹⁄₁₆ the amount of energy of its maximum voltage level of 2,200 volts, still resulting in substantially reduced energy requirements for self test from that of the prior art.

Figure 6:
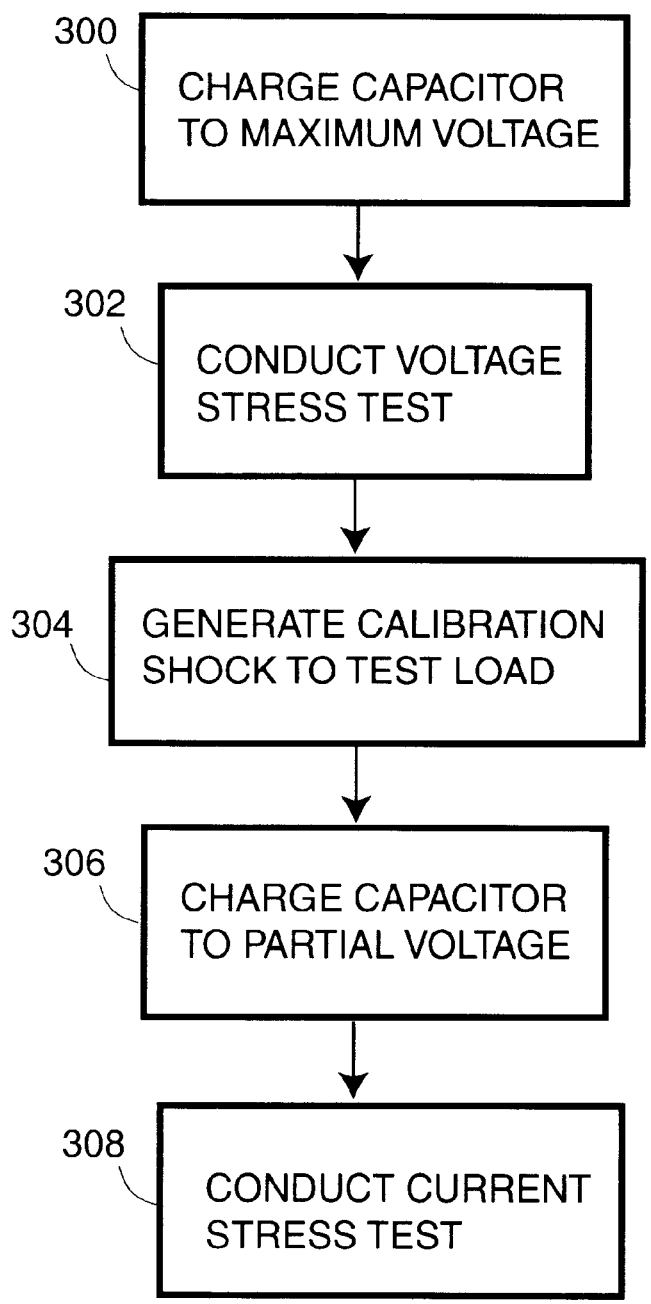
FIG. 6 is a flow chart of the self test method according to the present invention.

In FIG. 6, there is shown a flow chart of the self test method according to the present invention. In step 300 labeled CHARGE CAPACITOR TO MAXIMUM VOLTAGE, the capacitor 40 is charged by the high voltage charger 22 to the maximum voltage level. In the preferred embodiment, the maximum voltage is approximately 2,000 volts. The voltage level across the capacitor 40 is measured by the voltage measurement circuit 42 and fed back to the controller 26 as the voltage signal. If the voltage signal is within specification limits, the operation of the high voltage charger 22 and energy storage circuit 20 are determined to be normal by the controller 26.

In step 302 labeled CONDUCT VOLTAGE STRESS TEST, the SCRs 50–56 are exposed to the maximum voltage present in the capacitor 40. The switch 80*a–b* is placed in the upper position to short the cathodes of the SCRs 50 and 52 together and the IGBT 70 is turned on. The SCRs 50 and 52 form the top half of the H bridge and are tested first. The pull down resistors 66 and 68 operate to pull the junction to ground potential to impose the maximum voltage across each of the SCRs 50 and 52 presently in their off state and appearing as an open circuit.

Leakage current through the H bridge circuit is monitored during the voltage stress test. The voltage signal from the voltage measurement circuit 42 may alternatively be monitored for voltage drop in place of the current signal. If the SCRs 50 and 52 leak only negligible amounts of current, then they are deemed to have passed the voltage stress test. Next, one or both of the SCRs 50 and 52 is turned on, now imposing the maximum voltage across each of the SCRs 54 and 56 which form a bottom half of the H bridge and appear as open circuits. If the SCRs 54 and 56 leak only negligible amounts of current, they are deemed to have passed the voltage stress test. A failure of the voltage stress test occurs when any of the SCRs 50–56, or any other element of the H bridge, breaks down and begins to pass substantial amounts of current.

In step 304 labeled GENERATE CALIBRATION SHOCK TO TEST LOAD, the capacitor 40 is still fully charged from the step 302 and can provide the calibration pulse to the test load. The test load consists of the load resistor 78 in series with the resistor 60 in the disarm circuit. The calibration pulse is delivered by turning on the SCR 76 which completely discharged the capacitor 40 before turning off again. Alternatively, the test load may consist of an external load resistor put in place of the pair of electrodes 12 which is delivered by turning on the IGBT 70 and either the SCRs 50 and 56 or the SCRs 52 and 54. The discharge time across the test load which is a known resistance such as 10 ohms is measured by the controller 26 in order to calibrate the amount of energy delivered to the patient in the defibrillation pulse.

In step 306 labeled CHARGE CAPACITOR TO PARTIAL VOLTAGE, the capacitor 40 is charged to a partial voltage which is a fraction of the maximum voltage and is chosen so that the high voltage circuit can source the maximum current level to the short circuit given the series resistance of the resistor 60. The switch 80a–b is moved into the shorting position, effectively shorting the HV switch 16, with only the resistor 60 in the current path to obtain the desired test load resistance. As an example, to obtain a maximum current level of 100 A sourced from the HV circuit into the short during the current stress test with a series resistance for the resistor 60 chosen to be 5 ohms, the capacitor 40 would be charged to 500 volts.

In step 308 labeled CONDUCT CURRENT STRESS TEST, the current handling capability of the H bridge is tested at the maximum current level. Similar to the sequence for generating a biphasic defibrillation pulse, the current test pulse is created in both polarities. IGBT 70 is turned on followed by SCRs 50 and 56 during the first phase to source the maximum current through the short circuit test load. After a desired time duration, IGBT 70 is turned off followed by SCRs 50 and 56 to end the first phase. The IGBT 70 is again turned on, followed by SCRs 52 and 54 during the second phase to source the maximum current through the short circuit. After a desired time duration, IGBT 70 is again turned off followed by SCRs 52 and 54.

Alternatively, IGBT 70 is turned on followed by SCRs 50 and 54 during the first phase to source the maximum current through one side of the H bridge circuit which acts as a short circuit. After a desired time duration, IGBT 70 is turned off followed by SCRs 50 and 54. The IGBT 70 is again turned on, followed by SCRs 52 and 56 during the second phase to secure the maximum current through the other side of the H bridge circuit which acts as a short circuit. After a desired time duration, IGBT 70 is again turned off followed by SCRs 52 and 56.

The time duration of the first phase is preferably very short to minimize the energy lost from the capacitor 40. Following the first phase, the capacitor 40 is then charged back up to the partial voltage level. Since only a portion of the energy stored in the capacitor 40 has been discharged during the first phase depending on its duration, charging the capacitor 40 for the second phase should require a fraction of the energy needed for the first phase. A failure of the current stress test occurs when the H bridge fails to source the maximum current level for the desired time duration, either in the first or second phases.

An advantage of the current stress test according to the present invention is that the H bridge is exercised in the same manner as it would be during the delivery of a defibrillation pulse under normal operation to obtain a more realistic test. The same pairs of SCRs, either SCRs 50 and 56 or SCRs 52 and 54 are used to deliver the first and second phases of the current stress test as well as the first and second phases of the biphasic defibrillation pulse.

It will be obvious to those having ordinary skill in the art that many changes may be made in the details of the above-described preferred embodiments of the invention without departing from the spirit of the invention in its broader aspects. For example, the self test method may be readily applied to any configuration of the HV switch 16, such as a simpler switch topology that supports only monophasic defibrillation pulses. The energy storage circuit 20 may also be constructed using multiple capacitors. The current stress test consisting of steps 306 and 308 may be conducted before the voltage stress test and calibration consisting of steps 300–304 during the self test operation. Therefore, the scope of the present invention should be determined by the following claims.

What we claim as our invention is:

1. A method for self test in a defibrillator comprising:
   charging an energy storage circuit to maximum voltage;
   conducting a voltage stress test of a high voltage switch coupled to said energy storage circuit;
   charging said energy storage circuit to a partial voltage; and
   conducting a current stress test of said high voltage switch.

2. A method for self test in a defibrillator according to claim 1 further comprising, after conducting said voltage stress test, generating a calibration shock to a test load.

3. A method for self test in a defibrillator according to claim 1 wherein said high voltage switch comprises an H bridge.

4. A method for self test in a defibrillator according to claim 3 wherein said H bridge comprises four SCRs in an upper half and a lower half.

5. A method for self test in a defibrillator according to claim 4, said voltage stress test further comprising:
   imposing said maximum voltage across said top half of said H bridge; and
   imposing said maximum voltage across said bottom half of said H bridge.

6. A method for self test in a defibrillator according to claim 4, said current stress test further comprising:
   sourcing a maximum current through said test load in a first phase; and
   sourcing said maximum current through said test load in a second phase.

7. A method for self test in a defibrillator according to claim 1 further comprising monitoring a current through said high voltage switch.

8. A method for self test in a defibrillator according to claim 1 further comprising monitoring a voltage across said energy storage circuit.

9. A method for self test in a defibrillator according to claim 1 wherein said energy storage circuit comprises a capacitor.

10. A method for self test in a defibrillator according to claim 1 wherein said maximum voltage exceeds an operating voltage.

11. A method for self test in a defibrillator according to claim 1 wherein said maximum current exceeds an operating current.

12. A method for self test in a defibrillator comprising:
    charging an energy storage circuit to maximum voltage;
    conducting a voltage stress test of a high voltage switch coupled to said energy storage circuit;
    generating a calibration shock to a test load;
    charging said energy storage circuit to a partial voltage; and
    conducting a current stress test of said high voltage switch.

13. A method for self test in a defibrillator according to claim 12 wherein said high voltage switch comprises an H bridge.

14. A method for self test in a defibrillator according to claim 13 wherein said H bridge comprises four SCRs in an upper half and a lower half.

15. A method for self test in a defibrillator according to claim 12, said voltage stress test further comprising:
    imposing said maximum voltage across said top half of said H bridge; and
    imposing said maximum voltage across said bottom half of said H bridge.

16. A method for self test in a defibrillator according to claim 12, said current stress test further comprising:
   sourcing a maximum current through said test load in a first phase; and
   sourcing said maximum current through said test load in a second phase.

17. A method for self test in a defibrillator according to claim 12 further comprising monitoring a current through said high voltage switch.

18. A method for self test in a defibrillator according to claim 12 further comprising monitoring a voltage across said energy storage circuit.

19. A method for self test in a defibrillator according to claim 12 wherein said energy storage circuit comprises a capacitor.

20. A method for self test in a defibrillator according to claim 12 wherein said maximum voltage exceeds an operating voltage.

21. A method for self test in a defibrillator according to claim 12 wherein said maximum current exceeds an operating current.

22. A defibrillator with a self test operation requiring reduced energy, comprising:
   an energy storage circuit for storing energy to deliver a defibrillation pulse;
   an HV switch coupled to said energy storage circuit to selectively couple said defibrillation pulse to a pair of electrodes;
   a charging circuit coupled to energy storage circuit to charge said energy storage circuit to a desired voltage level; and
   a controller coupled to said energy storage circuit, said HV switch, and said charging circuit to control said self test operation;
   wherein said self test operation comprises a current stress test and a voltage stress test.

23. A defibrillator with a self test operation requiring reduced energy according to claim 22, said current stress test comprising charging said energy storage circuit to a partial voltage and sourcing current into a short circuit at a maximum current level.

24. A defibrillator with a self test operation requiring reduced energy according to claim 23, said current stress test further comprising sourcing said current into said short circuit in first and second phases.

25. A method for self test in a defibrillator according to claim 23 wherein said maximum current exceeds an operating current.

26. A defibrillator with a self test operation requiring reduced energy according to claim 22, said voltage stress test comprising charging said energy storage circuit to a maximum voltage and imposing said maximum voltage across said HV switch.

27. A method for self test in a defibrillator according to claim 22 wherein said maximum voltage exceeds an operating voltage.

28. A defibrillator with a self test operation requiring reduced energy according to claim 22 wherein said HV switch comprises an H bridge in series with an IGBT.

29. A defibrillator with a self test operation requiring reduced energy according to claim 28 wherein said H bridge comprises an SCR in each leg.

30. A defibrillator with a self test operation requiring reduced energy according to claim 22 wherein said HV switch further comprises a switch coupled to said H bridge which selectively couples a test load across said H bridge during said current stress test and said voltage stress test.

31. A defibrillator with a self test operation requiring reduced energy according to claim 22 wherein said HV switch further comprises a disarm circuit in parallel with said H bridge.

* * * * *